(12) United States Patent
Korzinov et al.

(10) Patent No.: US 10,772,521 B2
(45) Date of Patent: *Sep. 15, 2020

(54) BIOLOGICAL SIGNAL MANAGEMENT

(71) Applicant: Braemar Manufacturing, LLC, Conshohocken, PA (US)

(72) Inventors: Lev Korzinov, San Diego, CA (US); Eric Baumann, San Diego, CA (US)

(73) Assignee: BRAEMAR MANUFACTURING, LLC, Eagan, MN (US)

( * ) Notice: Subject to any disclaimer, the term of this patent is extended or adjusted under 35 U.S.C. 154(b) by 132 days.

This patent is subject to a terminal disclaimer.

(21) Appl. No.: 15/720,957

(22) Filed: Sep. 29, 2017

(65) Prior Publication Data

US 2018/0242870 A1  Aug. 30, 2018

Related U.S. Application Data

(63) Continuation of application No. 13/904,971, filed on May 29, 2013, now Pat. No. 9,775,534, which is a continuation of application No. 11/984,310, filed on Aug. 20, 2007, now abandoned, which is a continuation of application No. 10/770,702, filed on Feb. 2, 2004, now Pat. No. 7,587,237.

(51) Int. Cl.
*A61B 5/04* (2006.01)
*A61B 5/046* (2006.01)
*A61B 5/0464* (2006.01)
*A61B 5/0468* (2006.01)

(52) U.S. Cl.
CPC .......... *A61B 5/04012* (2013.01); *A61B 5/046* (2013.01); *A61B 5/0464* (2013.01); *A61B 5/0468* (2013.01)

(58) Field of Classification Search
CPC . A61B 5/0402; A61B 5/0452; A61B 5/04012; A61B 5/046; A61B 5/0464; A61B 5/0468
See application file for complete search history.

(56) References Cited

U.S. PATENT DOCUMENTS

| | | | | |
|---|---|---|---|---|
| 4,589,420 A | * | 5/1986 | Adams | A61B 5/04525 600/515 |
| 7,587,237 B2 | * | 9/2009 | Korzinov | A61B 5/046 600/509 |
| 9,775,534 B2 | * | 10/2017 | Korzinov | A61B 5/046 |

* cited by examiner

*Primary Examiner* — Eric D. Bertram
(74) *Attorney, Agent, or Firm* — Chang B. Hong, Esq.

(57) ABSTRACT

Systems and techniques for managing biological signals. In one implementation, a method includes receiving a cardiac biological signal that includes information describing events, determining a merit of each event based on one or more of a severity of a cardiac condition associated with the event and a quality of the event, and handling a subset of the events that meet a merit criterion. The subset can be handled for medical purposes.

12 Claims, 7 Drawing Sheets

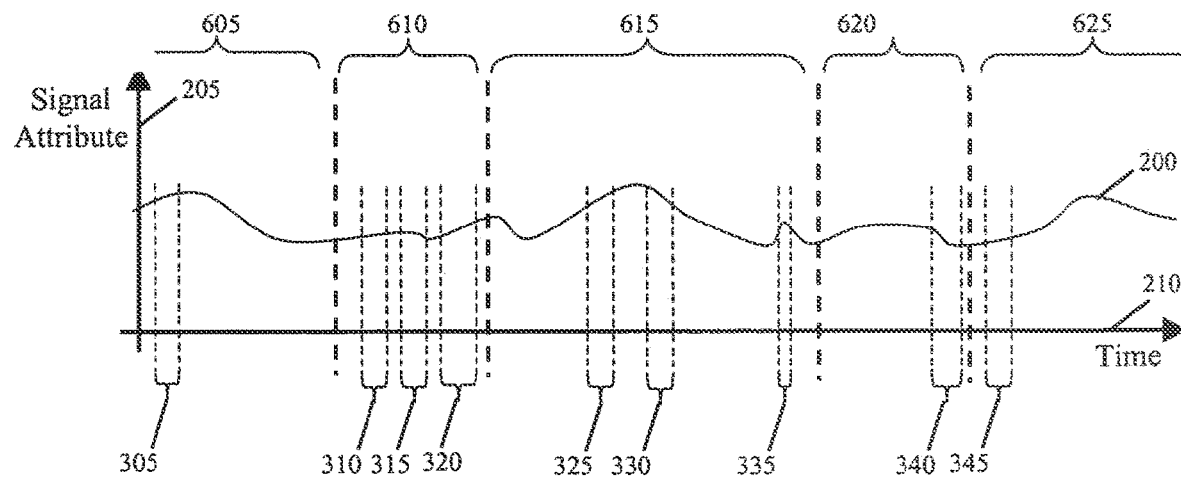
FIG. 6
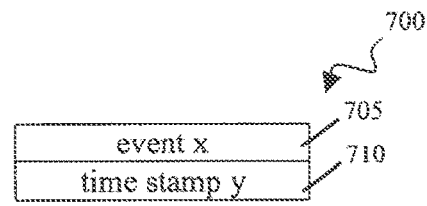
FIG. 7
| EVENT CATEGORY | category a |
|---|---|
| SPAN | span z |
| ALLOCATION | event 1<br>time stamp 1 |
| ALLOCATION | event 2<br>time stamp 2 |
| ALLOCATION | event 3<br>time stamp 3 |
FIG. 8

BIOLOGICAL SIGNAL MANAGEMENT

CROSS-REFERENCE TO RELATED APPLICATIONS

This application is a continuation of U.S. patent application Ser. No. 13/904,971 filed May 29, 2013 (pending), which is a continuation of U.S. patent application Ser. No. 11/894,310 filed Aug. 20, 2007 (abandoned), which is a continuation of U.S. patent application Ser. No. 10/770,702 filed Feb. 2, 2004 now U.S. Pat. No. 7,587,237, each of which are incorporated by reference herein in their entirety.

BACKGROUND

This disclosure relates to the management of biological signals.

Biological signals are electrical or optical streams that include information describing or otherwise relating to the state of a biological system. In the medical context, biological signals generally include information relating to the physiological state of an organism. Such information can be used to diagnose and treat disease states of the organism and can be gathered using any of a number of different techniques. Examples of such techniques include electrical potential measurements (e.g., electrocardiography (ECG's), electromyography, and electroencephalography), blood and other body fluid analyte measurements (e.g., pulse oximetry, blood glucose concentration, blood pH and other ion concentrations), and mechanical measurements (e.g., blood pressure measurements, heart sound transduction, height and weight measurements).

SUMMARY

The biological signal management systems and techniques described here may include various combinations of the following features.

In one aspect, a method includes receiving a cardiac biological signal that includes an event relevant to a medical purpose, determining a merit of the event for the medical purpose, associating the event with a time span in which the event occurred if the event's merit is among a certain number of the most meritorious events that occurred in the time span, and handling the association of the time span and the event.

The merit of the event can be determined by determining the severity and the quality of the event. The quality of the event can be determined by determining the noise in the event. An event can be received after the event has been separated from another portion of the cardiac biological signal. The event can also be identified within the received cardiac biological signal. The event can be one or more of an asystole event, a tachycardia event, a bradycardia event, and an atrial fibrillation/flutter event based on identifying characteristics of these events. The event can be identified based on a frequency of heart beats.

A category of the event can be determined. The event can be associated with the time span when the event merit places the event within the certain number of the most meritorious events of the category. The number of the most meritorious events can be predetermined. The association can be handled by generating a data structure having a time stamp associated with the event or by transmitting the association to a remote receiver. The event can have a greater relevance to a medical diagnostic purpose than an average relevance of the biological signal.

In another aspect, a method includes receiving a cardiac biological signal that includes information describing events, determining a merit of each event based on one or more of a severity of a cardiac condition associated with the event and a quality of the event, and handling a subset of the events that meet a merit criterion.

The subset can be handled for medical purposes. The merit criterion can be based on merits of other events. The merit of each event can be determined based on both the severity and the quality of the event. The subset can be the events that have merits among a certain number of the most meritorious and the subset can be the events that occur within a certain time span. For example, the time span can be predetermined. The subset of events can be transmitted to a remote medical receiver.

In another aspect, a method includes receiving a biological signal, identifying an event in the biological signal, determining a merit of the event for the certain purpose, comparing the merit of the event with a second merit of a second event to identify a more meritorious event, creating an episode describing the more meritorious event, associating the episode with a time span in which the events occurred, and transmitting the association of the episode and the time span to a remote receiver. The event can have a greater relevance for a certain purpose than an average relevance of the biological signal.

The episode can be associated with the time span by creating a data structure including the episode and a time stamp indicating when the event occurred. The episode can be created by redacting the more meritorious event. A category of the event can also be determined. The merit of the event can be compared with the second merit of the second event of the same category. The association of the episode and the time span can be associated with a collection of associations of episodes and time spans. The resulting collection of associations of episodes and time spans can be transmitted to the remote receiver.

These biological signal management systems and techniques may provide one or more of the following advantages. For example, the management of biological signals can facilitate a coherent approach to organization and presentation of the information contained in the biological signals. Such management must address various objectives that often oppose one another. For example, the volume of data often should be reduced to minimize data handling costs. At the same, relevant information should not be lost. These objectives are of importance in the medical context, where data review may be carried out by a physician or other trained personnel and hence may prove costly. On the other hand, discarding medically relevant information may hinder or even prevent appropriate diagnosis and/or treatment.

The described biological management systems and techniques can address these and other objectives by increasing the average relevance of data that is handled. Such reductions in data clutter can be used to quickly provide physicians with relevant information, decreasing the cost of data review and increasing the likelihood that diagnosis and/or treatment is appropriately delivered.

Another set of opposing objectives relates to the timing of data handling. In many data handling systems, continuous handling of data is simply too costly. On the other hand, batch handling that only occurs occasionally may result in improper delays. These objectives are also of importance in the medical context, where continuous data handling may be unnecessary or too costly, but delayed handling may endanger patients.

The described biological management systems and techniques can address these and other objectives by selecting the timing of data handling to accommodate both the realities of data handling and the need to ensure patient safety. For example, the timing of handling can be selected to ensure timeliness in any prophylactic or diagnostic efforts without requiring continuous processes.

The details of one or more implementations are set forth in the accompanying drawings and the description below. Other features, objects, and advantages will be apparent from the description and drawings, and from the claims.

DESCRIPTION OF DRAWINGS

FIGS. 5 and 6 show the biological signal of FIG. 2 divided into a collection of time spans.

FIGS. 7 and 8 show data structures that associate one or more events with a time span.

Like reference symbols in the various drawings indicate like elements.

DETAILED DESCRIPTION

Figure 1:
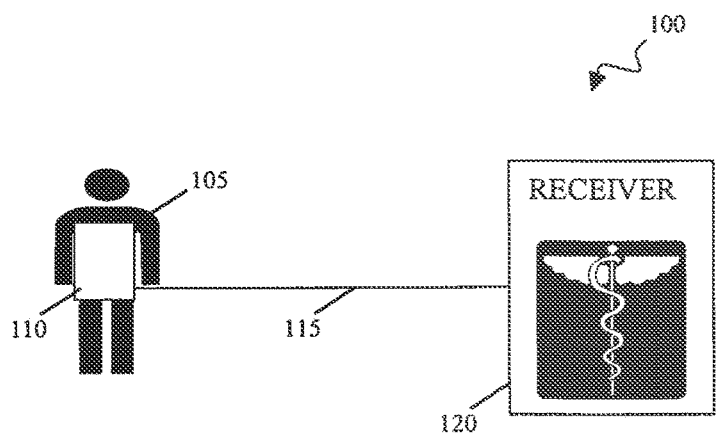
FIG. 1 shows a system in which a biological signal is monitored for medical purposes.

FIG. 1 shows a system 100 in which a biological signal derived from an individual is monitored for medical purposes. System 100 includes an individual 105, instrumentation 110, a signal path 115, and a receiver 120. Individual 105 can be a patient or a healthy individual for whom monitoring of one or more biological signals is deemed to be appropriate. Instrumentation 110 can include one or more sensing, calibration, signal processing, control, data storage, and transmission elements suitable for generating and processing the biological signal, as well as relaying all or a portion of the biological signal over path 115. Path 115 can be any suitable medium for data transmission, including wired and wireless media suitable for carrying optical and/or electrical signals. The receiver 120 can include a receiver element for receiving the transmitted signal, as well as various data processing and storage elements for extracting and storing the information carried by the transmission regarding the state of individual 105. The receiver 120 can be a medical system in that receiver 120 presents information to medical personnel or to a medical expert system for analysis. The receiver 120 either can reside remotely from instrumentation 110 in that receiver 120 is not located at the same site (e.g., at the same hospital, nursing home, or other medical care facility) as instrumentation 110 or the receiver 120 can reside within the same general area or vicinity as instrumentation 110 (e.g., within the same room, building, or health care facility).

Figure 2:
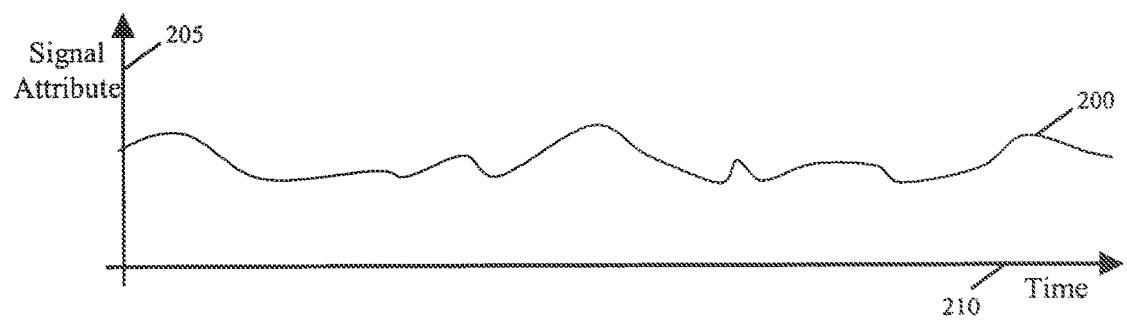
FIG. 2 shows an example biological signal.

FIG. 2 shows an example of a biological signal 200. The biological signal 200 is a time variant signal in that an attribute 205 of biological signal 200 changes with time 210. Attribute 205 of biological signal 200 may continuously change with time and may never reach a steady state value as activity level, metabolic rate, or other factors vary over the course of days, weeks, or even longer periods of time.

Figure 3:
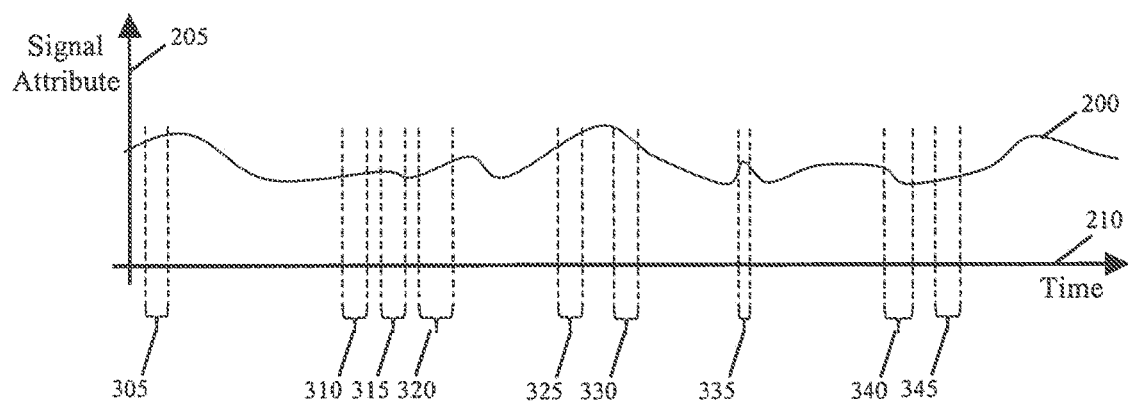
FIG. 3 shows a series of events in the biological signal of FIG. 2.

Although attribute 205 of biological signal 200 may change continuously, all of the changes may not have the same relevance to a particular purpose for which the biological signal 200 is monitored. FIG. 3 shows the biological signal 200 having a series of events 305, 310, 315, 320, 325, 330, 335, 340, 345 identified. Events 305, 310, 315, 320, 325, 330, 335, 340, 345 generally are periods in time 210 when the information content of biological signal 200 is deemed to be of increased relevance to a particular purpose for which biological signal 200 is monitored. Events 305, 310, 315, 320, 325, 330, 335, 340, 345 need not be of equal or predetermined duration. For example, event 335 is shorter than event 320 and the duration of these and other events can depend on the nature of the increased relevance to the particular purpose for which biological signal 200 is monitored.

The increased relevance of events 305, 310, 315, 320, 325, 330, 335, 340, 345 can be determined using a number of approaches. For example, events 305, 310, 315, 320, 325, 330, 335, 340, 345 can represent responses to known or controlled stresses on an organism.

Events 305, 310, 315, 320, 325, 330, 335, 340, 345 also can be identified based on characteristics of biological signal 200 and classified into categories based on the identifying characteristics. Tables 1 and 2 lists example categories of cardiac events and characteristics that can be used to identify the events. The characteristics identified in Tables 1 and 2 can be used to identify events during cardiac monitoring using electrocardiography.

Figure 4:
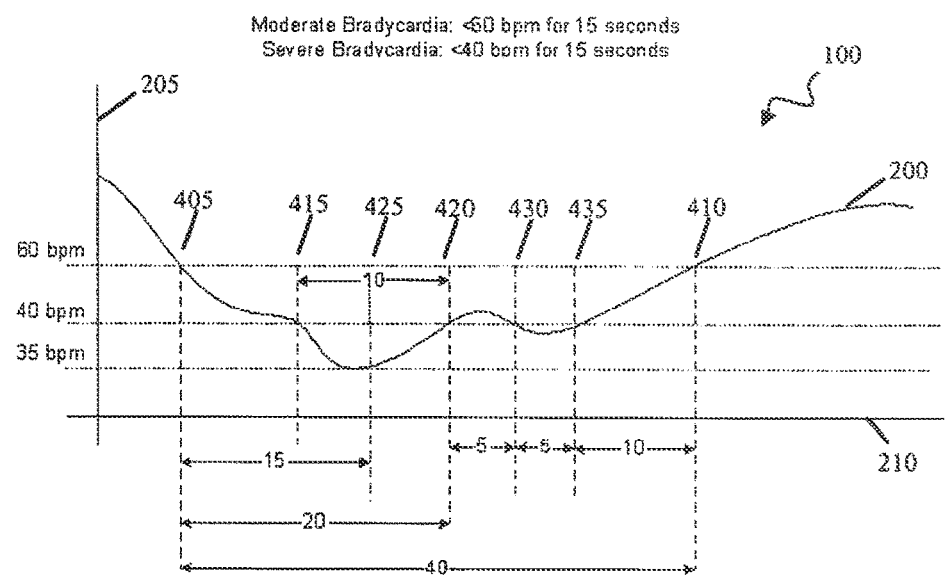
FIG. 4 illustrates how certain characteristics can be used to identify events.

FIG. 4 illustrates an example of how the characteristics identified in Table 1 can be used to identify cardiac events. In this example, the attribute 205 of biological signal 200 that changes with time 210 (shown in seconds) is heart rate (shown in beats per minute (bpm)). In the illustrated example, the predetermined heart rate for identifying Moderate Bradycardia is 60 bpm and the predetermined duration is 40 seconds. The predetermined heart rate for identifying Severe Bradycardia is 40 bpm and the predetermined duration is 15 seconds.

In FIG. 4, heart rate attribute 205 drops below 60 bpm at time 405, where it remains until

TABLE 1

| Event Category | Identifying Characteristic(s) | Duration |
|---|---|---|
| VFIB | Ventricular fibrillation | NA |
| Long Pause/ Asystole | No QRS detected for a predetermined duration. | e.g., 3 to 6 seconds |

TABLE 1-continued

| Event Category | Identifying Characteristic(s) | Duration |
|---|---|---|
| VTACH | Four or more V-beats in row and heart rate more than a predetermined value (e.g., 100 to 200 bpm). Not associated with a VFIB event | 4 V-beats |
| Patient initiated event | Patient indicates event is occurring | Patient selected |
| Severe Tachycardia | Heart rate over a predetermined time (e.g., 10 to 120 seconds) is greater than a predetermined value (e.g., 161 to 220 bpm) Not associated with a VTACH or a VFIB event | e.g., 10 to 120 seconds |
| Severe Bradycardia | Heart rate over a predetermined time (e.g., 10 to 120 seconds) is less than a predetermined value (e.g., 30 to 39 bpm) Not associated with an asystole or pause event | e.g., 10 to 120 seconds |
| Atrial Fibrillation/ Flutter with High HR | Heart rate greater than or equal to a predetermined value (e.g., 100 to 220 bpm) Associated with an Atrial Fibrillation/Flutter onset event | e.g., 10 to 120 seconds |
| Pause | No QRS complex for a predetermined duration (e.g., 2 seconds to duration of Long Pause/Asystole event) | e.g., 2 seconds to duration of Long Pause/Asystole event |
| Atrial Fibrillation/ Flutter onset | Irregular rhythm Not associated with a VTACH and VFIB event | e.g., 30 QRS complexes |
| Moderate Bradycardia | Heart rate for a predetermined duration (e.g., 10 to 120 seconds) is less than a predetermined value and greater than predetermined value in a severe bradycardia event (e.g., severe bradycardia value to 60 bpm) Not associated with an asystole, a pause, or a severe bradycardia event | e.g., 10 to 120 seconds |
| Moderate Tachycardia | Heart rate for a predetermined duration (e.g., 10 to 120 seconds) is greater than a predetermined value and less than predetermined value in a severe tachycardia event (e.g., 100 bpm to the severe tachycardia value) Not associated with a VTACH, a VFIB, or a severe tachycardia event | e.g., 10 to 120 seconds | time 410, 40 seconds later. The period between time 405 and time 410 can be identified as a Moderate Bradycardia event. In contrast, at time 415, heart rate attribute 205 drops below 40 bpm where it remains until time 420, ten seconds later. Heart rate attribute 205 also reaches a minimum of 35 bpm at a time 425. Despite reaching this minimum, the duration of the period between time 415 and time 420 (i.e., 10 seconds) is too short to be identified as a Severe

TABLE 2

| EVENT CATEGORY | IDENTIFYING CHARACTERISTICS | EXAMPLE IDENTIFYING THRESHOLD |
|---|---|---|
| TACHYCARDIA 1 - Severe Tachycardia 2 - Moderate Tachycardia | Sustained heart rate (e.g., heart rate for 10 to 120 seconds) exceeds a heart rate threshold | 1 - Sustained heart rate exceeds a High Heart Rate (HHR) threshold of 190 bpm 2 - Sustained heart rate exceeds a Low Heart Rate (LHR) threshold of 140 bpm |
| ATRIAL FIBRILLATION 1 - Atrial Fibrillation/ Flutter with High HR 2 - Atrial Fibrillation | Loss of synchrony between the atria and the ventricles (shown, e.g., by variability in beat-to-beat period) | 1 - Heart rate exceeds a Atrial Fibrillation High Heart Rate (AFHHR) threshold of 130 bpm 2 - No heart rate threshold |
| PAUSE 1 - Asystole 2 - Pause | No QRS detected for a specified threshold duration | 1 - No QRS for a high threshold of 4 seconds 2 - No QRS for a low threshold of 2 seconds |
| BRADYCARDIA 1 - Severe Bradycardia 2 - Moderate Bradycardia | Sustained heart rate (e.g., heart rate for 10 to 120 seconds) is below a specified threshold | 1 - Sustained heart rate is below a Low Heart Rate (LHR) threshold of 35 bpm 2 - Sustained heart rate is below a High Heart Rate (HHR) threshold of 40 bpm |

Bradycardia event. At time 430, heart rate attribute 205 again drops below 40 bpm, where it remains until time 435, five seconds later. The duration of the period between time 430 and time 435 is too short to be identified as a Severe Bradycardia event.

Figure 5:
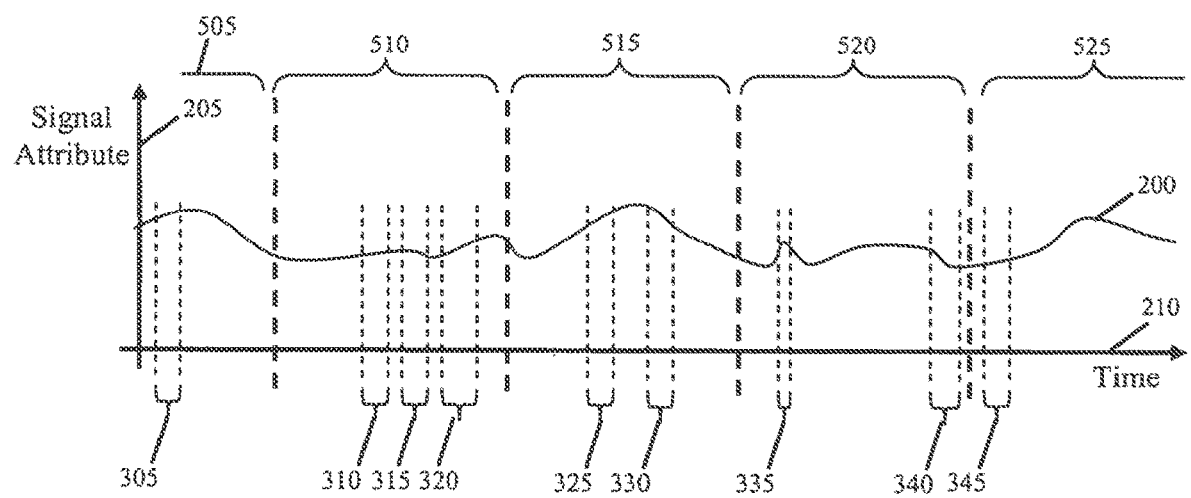

FIGS. 5 and 6 show that time 215 can be divided into a collection of time spans 505, 510, 515, 520, 525, 605, 610, 615, 620, 625. Spans 505, 510, 515, 520, 525, 605, 610, 615, 620, 625 can have equal durations (such as spans 505, 510, 515, 520, 525) or spans can be of variable durations (such as spans 605, 610, 615, 620, 625). In general, the duration of spans 505, 510, 515, 520, 525, 605, 610, 615, 620, 625 is proportional to the duration of the events sought to be identified. The duration of spans 505, 510, 515, 520, 525, 605, 610, 615, 620, 625 can be selected based on consideration of two or more factors, such as the number of events likely to occur in each span and the need to handle events for a particular purpose for which biological signal 200 is monitored. In particular, if spans 505, 510, 515, 520, 525, 605, 610, 615, 620, 625 are too short, then spans 505, 510, 515, 520, 525, 605, 610, 615, 620, 625 may lack an event. On the other hand, if spans 505, 510, 515, 520, 525, 605, 610, 615, 620, 625 are too long, then the delay in handling events may be too large. Such a delay may be particularly harmful in the medical context, where an excessive delay may hinder prophylactic or diagnostic efforts. In the context of cardiac monitoring, a span duration of between one half and four hours, such as between one and three hours or approximately two hours, is effective to address such considerations.

The duration of spans 505, 510, 515, 520, 525, 605, 610, 615, 620, 625 can also accommodate physiological rhythms of a biological system. For example, in cardiac monitoring, longer spans may be appropriate at night or periods of decreased activity and shorter spans may be appropriate during the day or periods of increased activity. The duration of spans 505, 510, 515, 520, 525, 605, 610, 615, 620, 625 can also be adjusted based on an attribute of biological signal 200. For example, in cardiac monitoring, the duration of spans 505, 510, 515, 520, 525, 605, 610, 615, 620, 625 can include a fixed number of beats rather than a fixed time period.

FIGS. 7 and 8 show data structures 700, 800 that associate one or more sample events with a span. Data structures 700, 800 can be used together or separately as alternative approaches to associating events with a span. Data structure 700 includes an event field 705 and a time stamp field 710. Event field 705 includes data describing a portion of a biological signal that has been identified as an event. Event field 705 can include raw data drawn from the biological signal or event field 705 can include an episode of an event to describe the event. An episode is a collection of information that summarizes the relevance of the event to the purpose for which the event is monitored. For example, an episode can be a redacted portion of an event (e.g., the first three minutes worth of the event). Time stamp field 710 includes data describing the time when the event described in event field 705 occurred. Time stamp field 710 can thus associate the event with a span by identifying a time that falls within the time span.

Data structure 800 is shown as a table of attribute-value pairs but other data structures (including, for example, records, files, lists, and other data structures) that associate similar information can be used. Data structure 800 includes an event category information field 805, span identification information field 810, and allocation information fields 815, 820, 825. Event category information field 805 describes one or more event categories that are allocable to data structure 800. An event category can be described by name, by an associated identification number or other token, or by a pointer or other description of a memory location that includes such information. Span identification information field 810 describes the time span from which events of a category identified in event category information field 805 are allocable to data structure 800. The time span can be described directly using, e.g., a start and stop time stamp, or the time span can be described indirectly by a pointer or other description of a memory location that includes such information. Each instance of data structure 800 can be specific to a single span.

Allocation information fields 815, 820, 825 each describe a certain event that is allocated to data structure 800. An event can be allocated to data structure 800 when the event is of a category described in event category information field 805 and when the event occurred in a time span described in span identification information field 810. Such allocations thus associate the event with the described category and time span. Allocation information fields 815, 820, 825 can describe an event by including an event field and a time stamp field, such as fields 705, 710 of data structure 700 (FIG. 7).

Data structure 800 can include one or more allocation information fields. Single allocation fields decrease the size of data structure 800 and may facilitate handling. Multiple allocation fields increase the number of events associated with the span identified by span identification information field 810 and may provide more complete information when data structure 800 is handled.

Figure 9:
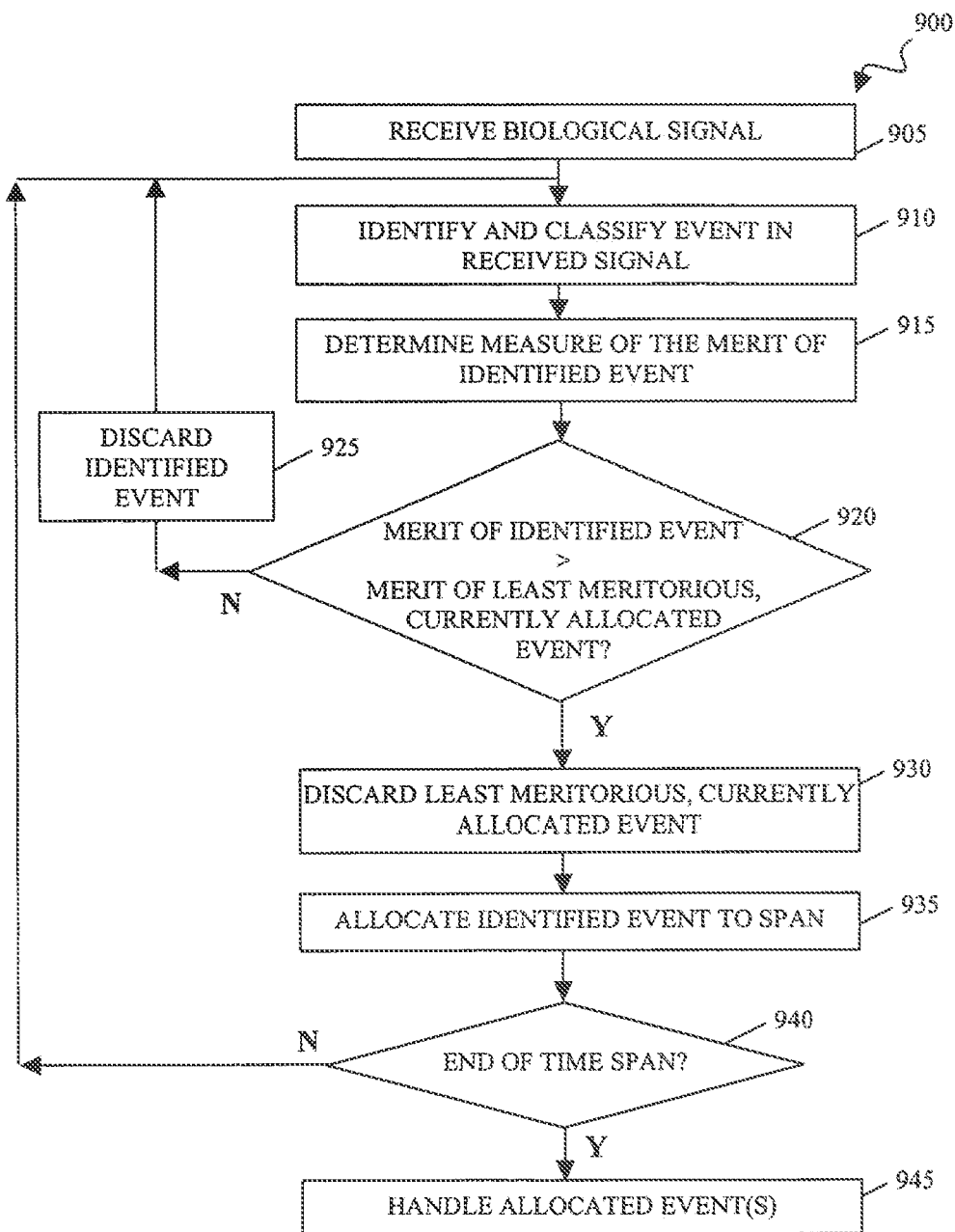
FIG. 9 shows a process in which events are associated with a time span.

FIG. 9 shows a process 900 in which events are associated with a time span. Events can be associated with a time span by allocation to a data structure such as data structures 700, 800. The process 900 can be performed by one or more data processing devices that perform data processing activities. The activities of process 900 can be performed in accordance with the logic of a set of machine-readable instructions, a hardware assembly, or a combination of these and/or other instructions. The device performing process 900 can be deployed at any of a number of different positions in a system in which a biological signal is monitored. For example, in system 100 (FIG. 1), the device performing process 900 can be deployed at instrumentation 110 or at receiver 120.

The device performing process 900 receives the biological signal at 905. The biological signal can be received in raw form or after signal processing. The biological signal can be received in digital or analog format. The receiving device can identify and classify one or more events in the biological signal at 910. Events can be identified and classified based on one or more attributes of the biological signal, such as the identifying characteristics described in Table 1.

The device performing process 900 can also determine a measure of the merit of identified events at 915. A measure of the merit of an event is a valuation of an event when applied to a particular purpose. For example, when the biological signal is monitored for diagnostic medical purposes, the measure of the merit of an event can describe the diagnostic value of the information content of the event. The measure of the merit of an event can be based on a number of factors, including whether or not the event is representative of the biological signal or of other events of the same category in the biological signal, the quality (e.g., noise or signal dropout) associated with the event, and even the category of the event itself.

The device performing process 900 can determine if the measure of the merit of an event identified at 910 is greater than the measure of the merit of the least meritorious event of the same category currently associated with the time span that includes the identified event at decision 920. The least meritorious event of the same category can be associated with the time span in a data structure such as data structures 700, 800 (FIGS. 7 and 8). The determination can be made by comparing the measure of the merit of the identified event with the measure of the merit of the associated, least meritorious event of the same category. If the identified event is not as meritorious, the device performing process 900 can discard the identified event at 925.

On the other hand, if the identified event is more meritorious than the associated, least meritorious event of the same category, then the device performing process 900 can discard the latter at 930 and associate the more meritorious event identified at 910 with the time span at 935. For example, the device performing process 900 can allocate the more meritorious event identified at 910 to the appropriate of fields 715, 805, 810 in data structures 700, 800 (FIGS. 7 and 8).

The device performing process 900 can determine if the end of a time span in the biological signal has been reached at decision 940. If the end of the span has not been reached, the process 900 returns to 910 to identify and classify any additional event(s) in the biological signal. If the end of the span has been reached, the process proceeds to handle the allocated events at 945. The events can be handled alone or in association with other information, including duration and classification information, prior and subsequent events of the same or different categories, and additional information retrieved from other biological signals.

TABLE 3

| Event Category | Event Grade |
|---|---|
| VFIB | 1 |
| Long Pause/Asystole | 1 |
| VTACH | 1 |
| Patient initiated event | 1 |
| Severe Tachycardia | 1 |
| Severe Bradycardia | 1 |
| Atrial Fibrillation/Flutter with High HR | 2 |
| Pause | 2 |
| Atrial Fibrillation/Flutter onset | 2 |
| Moderate Bradycardia | 2 |
| Moderate Tachycardia | 2 |

Figure 10:
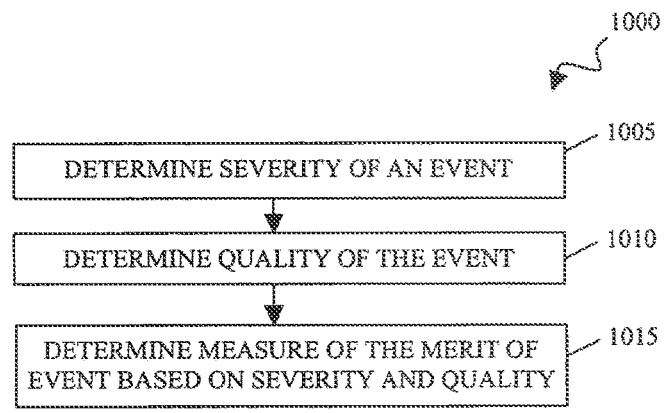
FIG. 10 shows a process for determining a measure of the merit for an event.

FIG. 10 shows a process 1000 for determining a measure of the merit of an event. A data processing device can perform the process 1000 in isolation or as part of a larger process. For example, the process 1000 can be performed within process 900 at 915 (FIG. 9). The device performing process 1000 can determine the severity of an event at 1005. The severity of an event is a measure of the gravity of the event to the purpose for which the biological signal is monitored. For example, when the biological signal is monitored for diagnostic medical purposes, the severity of an event can be indicative of the individual's physical discomfort or hardship associated with a diagnosis that can be made using the event. Severity can be graded on a discrete scale or on a continuous scale. Table 3 shows example discrete grades of the severity of various cardiac events when cardiac monitoring is performed for prophylactic and diagnostic purposes. In Table 3, events are graded on a two point scale, with an event grade of "1" indicating that the event is more severe and an event grade of "2" indicating that the event is less severe (e.g., a moderately sever event). For example, event grade "1" can indicate an acute medical condition that requires immediate medical attention, whereas event grade "2" can indicate a chronic or other medical condition that does not require immediate medical attention.

Another approach to determining the severity of an event involves comparing characteristics of the biological signal during the event with threshold values relating to various physiological conditions associated with the events. For example, for a tachycardia event as described in Table 2, the severity of a tachycardia event can be determined using Equation 1:

$$\text{Tachy Severity} = (\text{Heart Rate} - \text{Low Heart Rate}/\text{High Heart Rate} - \text{Low Heart Rate}) \quad \text{Equation 1}$$

Similarly, the severity of a Bradycardia event, and Atrial Fibrillation Event, and a Pause event can be determined using the appropriate of Equations 2-4:

$$\text{Brady Severity} = (\text{High Heart Rate} - \text{Low Heart Rate})/(\text{High Heart Rate} - \text{Low Heart Rate}) \quad \text{Equation 2}$$

$$\text{AFIB Severity} = \text{Heart Rate}/\text{Atrial Fibrillation High Heart Rate} \quad \text{Equation 3}$$

$$\text{Pause Severity} = (\text{Pause Duration} - \text{Low Threshold})/(\text{High Threshold} - \text{Low Threshold}) \quad \text{Equation 4}$$

The device performing process 1000 can also determine the quality of the event at 1010. The quality of the event is a measure of the likelihood that the event is suited to the purpose for which the biological signal is monitored. One factor that can impact quality is the amount or type of noise in the biological signal during the event. For example, when the biological signal is a cardiac signal monitored for diagnostic medical purposes, noise can be determined using approaches such as those described in Wang, J. Y. "A New Method for Evaluating ECG Signal Quality for Multi-lead Arrhythmia Analysis," appearing in Proceedings of IEEE Computers in Cardiology Conference 2002, pp. 85-88 and U.S. Pat. No. 5,967,994 to Jyh-Yun Wang, the contents of both of which are incorporated herein by reference. Quality can be graded on a discrete scale or on a continuous scale.

TABLE 4

| Severity | Noise | Quality |
|---|---|---|
| Low | High | Lowest |
| Low | Medium | Low |
| Low | Low | Low |
| Medium | High | Low |
| Medium | Medium | Medium |
| Medium | Low | High |
| High | High | Low |
| High | Medium | High |
| High | Low | High |

The device performing process 1000 can determine the measure of the merit of an event based at least in part on the severity and quality of the event at 1015. The measure of the merit can be graded on a discrete scale or on a continuous scale. The measure of the merit can be determined using any of a number of different approaches. Table 4 includes examples of various discrete merit grades (lowest, low, medium, and high) that can be assigned to an event when an event is determined to have the corresponding severity and quality.

The handling of allocated events, such as those allocated during a process such as process 900, can involve any of a number of different activities. For example, event handling can include notifying medical personnel about the event. Such notification can be performed in response to the identification of an event associated with an acute medical condition, such as those events graded level "1" in Table 3. Event handling can also include the assembly of more complex data structures, the transmission of allocated events to, for example, a receiver such as receiver 120 (FIG. 1), or the storage of allocated events (for example, in anticipation of assembly into more complex data structures or transmission). Such data structure assembly, transmission, and storage can be performed with events associated with medical conditions that do not require immediate medical attention, such as those graded level "2" in Table 3.

Figure 11:
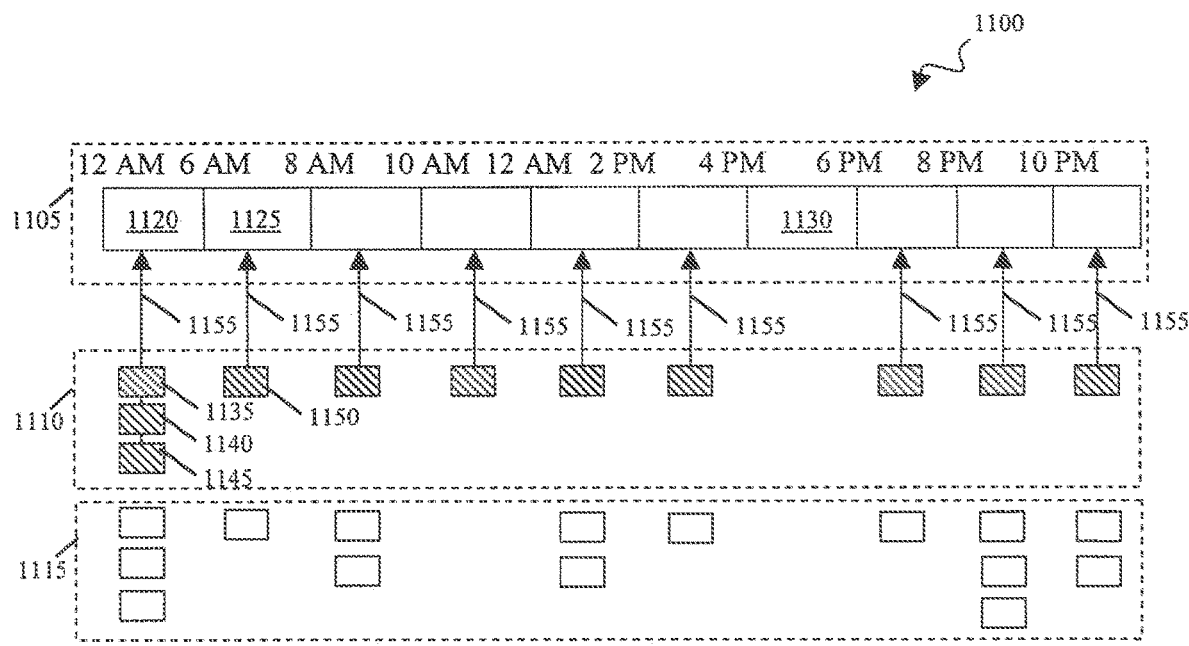
FIG. 11 shows a data structure that can result from handling of events associated with time spans.

FIG. 11 shows a data structure 1100 that can result from handling of events associated with time spans. The events and time spans can be associated by repeated performance of process 900 by a data processing device. Data structure 1100 includes a data assembly 1105, a series of associated events 1110, and a series of discarded events 1115. Data assembly 1105 includes a collection of time span records, including time span records 1120, 1125, and 1130. Time span records 1120, 1125, 1130 can include information identifying the duration of an associated time span. For example, time span record 1120 can include information identifying that span record 1120 lasts from 12 AM to 6 AM, whereas time span record 1130 can include information identifying that span record 1130 lasts from 4 PM to 6 PM. Time span records 1120, 1125, 1130 can include information identifying one or more categories of events associated with time span records 1120, 1125, 1130, as well as a severity of any associated category of events. For example, data structure 1100 can be devoted to events of a certain severity, such as level 2 events as discussed above.

Associated events 1110 includes a collection of event records of one or more categories, including event records 1135, 1140, 1145, 1150. Associated events 1110 can be allocated to the time spans in data assembly 1105 by allocation to an appropriate time span record. Event records can include data describing the event (such as raw data from the relevant portion of biological signal 200). Associated events 1110 can be allocated to the appropriate time span records through a series of pointers 1155. For example, event records 1135, 1140, 1145 are allocated to time span record 1120 through a first pointer 1155, whereas event record 1150 is associated with time span record 1125 through a second pointer 1155. A time span record need not have an associated event record. For example, no event record is associated with time span record 1130. This lack can reflect that no appropriate event was identified within the time span associated with time span record 1130.

Discarded events 1115 includes a collection of event records of one or more categories. Discarded events 1115 are not associated with the time spans in data assembly 1105 or with any of allocated events 1110.

Figure 12:
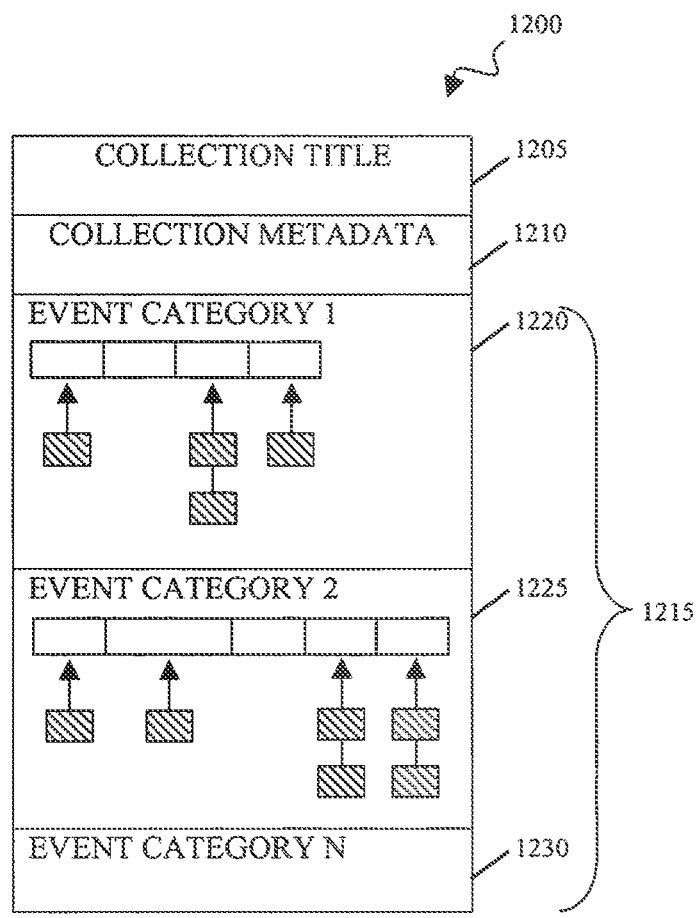
FIG. 12 shows a data assembly that can result from handling of events associated with time spans.

FIG. 12 shows another data assembly, namely a data collection 1200, that can result from handling of events associated with time spans. Data collection 1200 includes a data collection title 1205, data collection metadata 1210, and a series of data structures 1215. Data collection title 1205 can include information identifying data collection 1200. Data collection metadata 1210 can include information about the data in collection 1200, such as the subject of the biological signal, parameters regarding the instrument used to generate the biological signal, and date and location information regarding the data generation process.

Series of data structures 1215 includes data structures 1220, 1225, 1230. Each data structure 1220, 1225, 1230 can result from associating events of different categories with time spans and can include one or more events of different categories. For example, each data structure 1220, 1225, 1230 can include a data structure such as data structure 1100. Since each data structure 1220, 1225, 1230 can include events from different categories selected for high information content, data collection 1200 can include a relatively large amount of information regarding a biological signal but yet retain a high density of information content.

Figure 13:
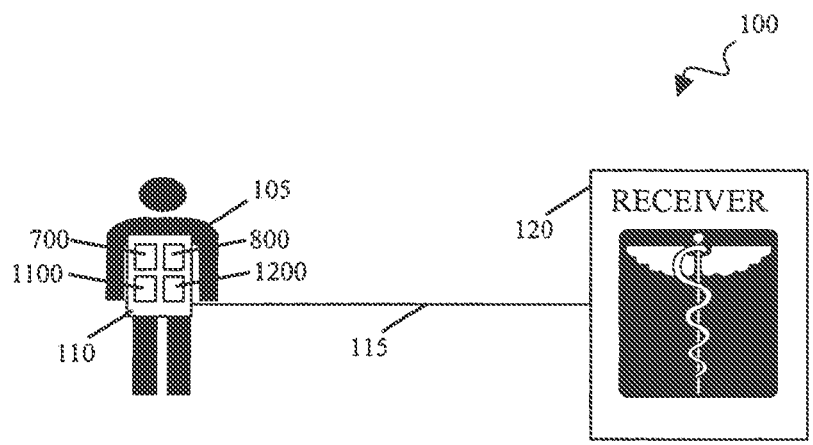
FIGS. 13 and 14 illustrate the handling of events associated with time spans by transmission to a receiver.
Figure 14:
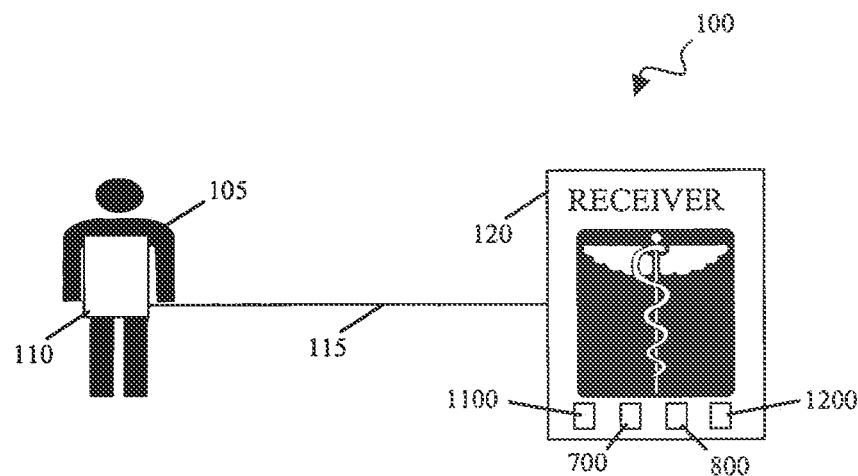

FIGS. 13 and 14 illustrate another way that events associated with time spans are handled, namely by transmission to a receiver in a system such as receiver 120 in system 100. In particular, as shown in FIG. 13, data can be gathered and events can be allocated at instrumentation 110 to form one or more of assemblies of data such as data structures 700, 800, 1100 and data collection 1200. In response to a trigger, data assemblies can be relayed over path 115 to receiver 120, where they are received as shown in FIG. 14. Example triggers include the passage of a predetermined period of time, user input indicating that transmission is appropriate, or the identification of an event of sufficient severity to warrant immediate transmission.

Figure 15:
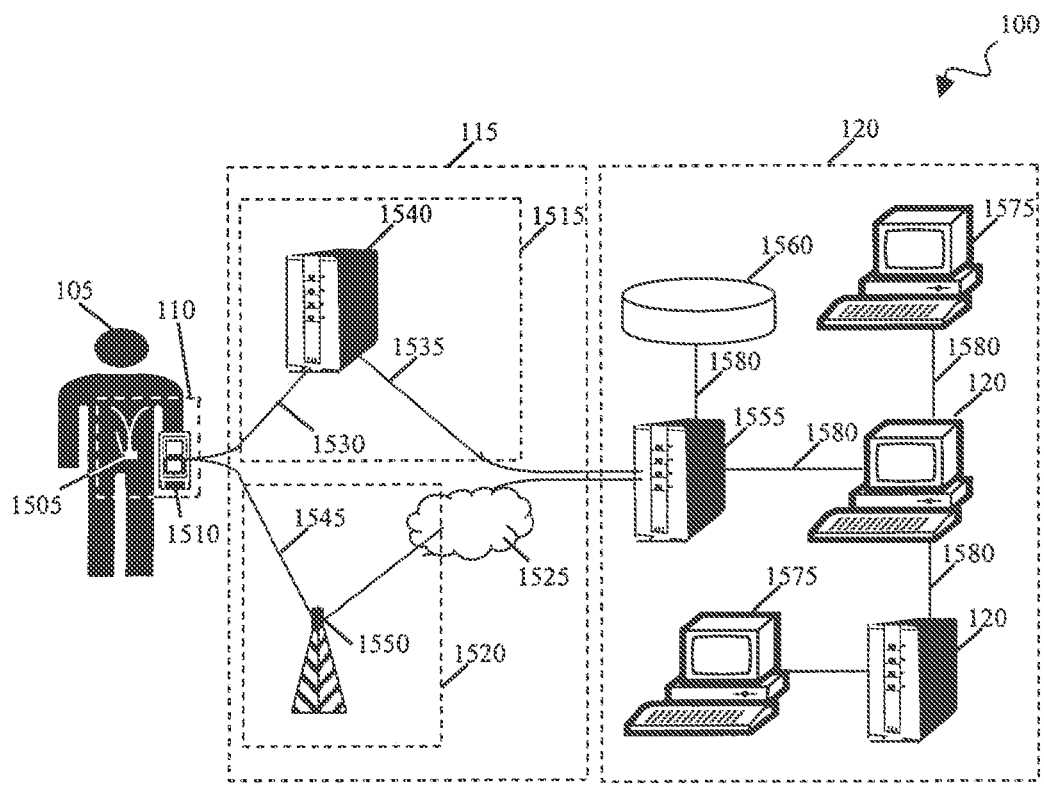
FIG. 15 shows a system in which events associated with time spans are handled by transmission to a receiver.

FIG. 15 shows one implementation of system 100 in which a biological signal derived from an individual is monitored for medical purposes. System 100 includes individual 105, instrumentation 110, signal path 115, and receiver 120.

Instrumentation 110 can be adapted for electrocardiographic monitoring of individual 105. Instrumentation 110 can include a sensor module 1505 and a monitor module 1510. Sensor module 1505 can include three ECG leads with electrodes, as well as a two channel ECG signal recorder and a wireless and/or wired data output. Sensor module 1505 can also include a clip for attaching sensor module to a belt, a neckpiece, or other item worn by individual 105. Monitor module 1510 includes a data input that is adapted to receive data output from sensor module 1505 as well as one or more wireless and/or wired data outputs for data communication over signal path 115. Monitor module 1510 also includes a data processing device that performs data processing activities in accordance with the logic of a set of machine-readable instructions. The instructions can be realized in digital electronic circuitry, integrated circuitry, specially designed ASICs (application specific integrated circuits), computer hardware, firmware, software, and/or combinations thereof. The instructions can describe how to identify and/or handle events in accordance with one or more of the techniques described herein. In one implementation, monitor module 1510 also includes an input/output device for interaction with a user (such as an event trigger input with which a user can manually trigger the start of an event.

Signal path 115 can include one or both of a wired data link 1515 and a wireless data link 1520 coupled to a data network 1525 to place instrumentation 110 in data communication with receiver 120. Wired data link 1515 includes a public network portion 1530 and a private or virtual private network portion 1535 bridged by a server 1540. Public network portion 1530 provides for data communication between instrumentation 110 and server 1540 over a wired data link such as a telephone network. Private network portion 1535 provides for private or virtually private data communication from server 1540 to receiver 120. Server 1540 can interface for data communication with both portions 1530, 1535. For example, server 1540 can communicate directly with receiver 120 using the peer-to-peer protocol (PPP).

Wireless data link 1545 can include one or more wireless receivers and transmitters 1550 such as a WiFi receiver, a cellular phone relay station, and/or other cellular telephone infrastructure to place instrumentation 110 in data communication with data network 1525. In turn, data network 1525 communicates with receiver 120.

Receiver 120 includes a receiver server 1555, a data storage device 1560, a call router 1565, a communications server 1570, and one or more application servers 1575 that are all in data communication with one another over one or more data links 1580. Receiver server 1555 is a data processing device that receives and transmits communications over signal path 115 and relays incoming communications to data storage device 1560 and call router 1565 in accordance with the logic of a set of machine-readable instructions. Data storage device 1560 is a device adaptable for the storage of information. Data storage device 1560 can be a volatile and/or non-volatile memory that records information electrically, mechanically, magnetically, and/or optically (such as a disk drive). Call router 1565 is a data processing device that, in accordance with the logic of a set of machine-readable instructions, identifies the content of an incoming communication and directs the communication to one or more appropriate application servers 1575 based on that content. Communications server 1570 is a data processing device that relays communications between call router 1565 and one or more application servers 1575 over an external network. Application servers 1575 are data processing devices that interact with a user or operate in isolation to provide one or more monitoring services in accordance with the logic of a set of machine-readable instructions. Data links 1580 can be part of a local area and/or private network or part of a wide area and/or public network.

In operation, sensor module 1505 can sense, amplify, and record electrical signals relating to the activity of the heart. Sensor module 1505 can also relay all or a portion of those signals to monitor module 1510 where they can be managed. For example, monitor module 1510 can manage the signals in accordance with one or more of processes 900 and 1000 (FIGS. 9-10). As part of the management, monitor module 1510 can transmit the signals to receiver 120. The signals can be transmitted in association with a time span. For example, the signals can be transmitted in one or more of data structures 700, 800, 1100, 1200 (FIGS. 7-8 and 11-12).

The transmitted signals pass along data link 115 over one or more of wired data link 1515 and wireless data link 1520 to receiver 120. At receiver 120, the signals are received by server 1555 which causes at least a portion of the incoming signals to be stored on data storage device 1560 and relayed to call router 1565. The incoming signals stored on data storage device 1560 can be stored in one or more of data structures 700, 800, 1100, 1200 (FIGS. 7-8 and 11-12).

The incoming signals relayed to call router 1565 are directed to one or more appropriate application servers 1575 based on the content of the signals. For example, when the signal relates to a certain category of cardiac event, the signal can be directed to a certain application server 1575 that is accessible to a cardiologist having expertise with that certain category of event. As another example, when the signal originates with an individual who is under the care of a particular physician, the signal can be directed to a certain application server 1575 that is accessible to that physician. As yet another example, when the signal relates to a certain category of cardiac event, the signal can be directed to a certain application server 1575 that accesses an expert system or other set of instructions for diagnosing and/or treating that category of event. When appropriate, a signal can be routed to communications server 1570 which in turn relays the signal to the appropriate application server 1575 over an external network.

Communications can also be relayed from receiver 120 back to individual 105 or to other individuals. For example, when a physician or expert system identifies that care is needed, a message requesting that the individual seek care can be returned to individual 105 over data link 115. In urgent care situations, third parties such as medical personnel can be directed to individual 105, either by receiver 120 or by instrumentation 110.

Various implementations of the systems and techniques described here can be realized in digital electronic circuitry, integrated circuitry, specially designed ASICs (application specific integrated circuits), computer hardware, firmware, software, and/or combinations thereof. These various implementations can include one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) may include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing environment that includes a back-end component (e.g., as a data server), or that includes a middleware component (e.g., an application server), or that includes a front-end component (e.g., a client computer having a graphical user interface or a Web browser through which a user can interact with an implementation of the systems and techniques described here), or any combination of such back-end, middleware, or front-end components. The components of the environment can be interconnected by any form or medium of digital data communication (e.g., a communication network). Examples of communication networks include a local area network ("LAN"), a wide area network ("WAN"), and the Internet.

The computing environment can include clients and servers. A client and server are generally remote from each other and typically interact through a communication network. The relationship of client and server arises by virtue of computer programs running on the respective computers and having a client-server relationship to each other.

A number of implementations have been described. Nevertheless, it will be understood that various modifications may be made. For example, information included in any of the data structures can be handled as meta data describing the data structures themselves and hence still associated with the data structures. An event can be associated with a time span based on the merit of the event exceeding a certain threshold. All events that exceed such a threshold can remain associated with the time span, rather than be discarded. Accordingly, other implementations are within the scope of the following claims.

What is claimed is:

1. A method comprising:
    receiving a cardiac biological signal that includes an event relevant to a medical purpose;
    determining a first measure of medical relevance of information describing a first cardiac event for a medical purpose;
    determining whether the first measure of medical relevance is greater than a threshold level of medical relevance, wherein a second cardiac event is currently allocated to a first data structure of a plurality of data structures, wherein a span identification field of a data structure identifies a first time span, and
    based on determining that the first measure of medical relevance is greater than the threshold level of medical relevance, allocating the first cardiac event to the first data structure;
    wherein each data structure of the plurality of data structures comprises:
        a span identification information field which identifies a time span, the time span having a duration, and
        an allocation information field describing a cardiac event allocated to the data structure, wherein the described cardiac event occurred within the time span identified in the span identification field.

2. The method of claim 1, wherein determining the medical relevance of the event comprises:
    determining a severity of the event; and
    determining a quality of the event.

3. The method of claim 2, wherein determining the quality of the event comprises determining the noise in the event.

4. The method of claim 1, wherein receiving the cardiac biological signal comprises receiving the event after the event has been separated from another portion of the cardiac biological signal.

5. The method of claim 1, further comprising identifying the event within the received cardiac biological signal.

6. The method of claim 1, wherein determining the measure of medical relevance of the event comprises identifying one or more of an asystole event, a tachycardia event, a bradycardia event, and an atrial fibrillation/flutter event based on identifying characteristics of these events.

7. The method of claim 6, wherein determining the measure of medical relevance of the event comprises identifying the event based on a frequency of heart beats.

8. The method of claim 1, wherein:
    the method further comprises determining a category of the event; and
    determining whether the measure of medical relevance of the information describing the event is greater than a threshold level of medical relevance comprises determining whether the medical relevance of the event places the event within a certain number of the most relevant events of the category.

9. The method of claim 1, wherein determining whether the measure of medical relevance of the information describing the event is greater than a threshold level of medical relevance comprises determining whether the medical relevance of the event is among a predetermined number of the most relevant events.

10. The method of claim 1, wherein allocating the event to the data structure comprises generating a data structure having a time stamp associated with the event.

11. The method of claim 1, wherein allocating the event to the data structure comprises transmitting to a remote receiver.

12. The method of claim 1, wherein the event has a greater relevance to a medical diagnostic purpose than an average relevance of a biological signal.

* * * * *